United States Patent [19]
Strini et al.

[11] 3,935,286
[45] Jan. 27, 1976

[54] PROCESS FOR REDUCING THE AMOUNT OF TRICHLOROETHYLENE IN 1,2-DICHLOROETHANE

[75] Inventors: Jean-Claude Strini, St-Auban; Jean-Raymond Costes, Dampierre, both of France

[73] Assignee: Rhone-Progil, Courbevoie, France

[22] Filed: Dec. 21, 1973

[21] Appl. No.: 427,374

[30] Foreign Application Priority Data
Dec. 27, 1972 France ............................. 72.46391

[52] U.S. Cl. ........................... 260/652 P; 260/656 R
[51] Int. Cl.² .................. C07C 17/38; C07C 19/00; C07C 21/06
[58] Field of Search .............................. 260/652 P

[56] References Cited
FOREIGN PATENTS OR APPLICATIONS
1,098,154   1/1968   United Kingdom ............. 260/652 P

*Primary Examiner*—D. Horwitz

[57] ABSTRACT

A process for converting trichloroethylene present in 1,2-dichloroethane by chlorination of the trichloroethylene in the liquid phase in the absence of light and in the presence of a Lewis acid catalyst wherein chlorine, 1,2-dichloroethane containing trichloroethylene and ethylene are introduced to a homogeneous reaction zone, with the mole ratio of ethylene to trichloroethylene being at least 50 and the mole ratio of trichloroethylene to chlorine being a maximum of 0.02.

7 Claims, No Drawings

PROCESS FOR REDUCING THE AMOUNT OF TRICHLOROETHYLENE IN 1,2-DICHLOROETHANE

The present invention relates to a process for reducing the amount of trichloroethylene which is present as an impurity in 1,2-dichloroethane, to values which are sufficiently low to eliminate any harmful influence which it can have on the thermal dissociation reaction of 1,2-dichloroethane when preparing vinyl chloride.

In a large number of modern industrial processes, it is known that the preparation of vinyl chloride is based on the thermal dissociation of 1,2-dichloroethane. Generally, this dichloroethane is produced by chlorination of ethylene in liquid phase and by oxychlorination of ethylene in vapor phase by means of a gas containing oxygen and hydrochloric acid, which comes from said thermal dissociation and/or any other source.

A certain number of by-products which may be found in the dichloroethane to be cracked result either from the thermal dissociation reaction or from the manufacture of dichloroethane, causing coaking of the cracking furnace which is more rapid than in the case of pure dichloroethane. Among such by-products, the main one to be noted is trichloroethylene as not only does it increase the speed of coaking but moreover it reduces the rate of conversion of dichloroethane to vinyl chloride. This trichloroethylene is virtually inseparable from the dichloroethane by conventional distillation means since it forms an azeotrope with dichloroethane, the boiling point of which is very close to that of dichloroethane. Moreover, the trichloroethylene is virtually not converted in the thermal dissociation operation. Consequently, even if the initial concentration of trichloroethylene is low, recycling the unconverted dichloroethane results in a substantial increase in the initial trichloroethylene concentration. It is therefore necessary to find a way of removing the trichloroethylene which is present in the dichloroethane.

It is known that such elimination can be effected by chlorination of trichloroethylene. In French Pat. No. 1,466,058, trichloroethylene is removed by treating raw dichloroethane by means of chlorine in the presence of a small amount of chlorination initiating agents, the most frequently used of which is ferric chloride. The trichloroethylene is then converted into pentachloroethane which can easily be separated subsequently by distillation. However, such a treatment suffers from at least two disadvantages: The investment required in a chlorination apparatus with all its accessories, comprising a system for removing the residual chlorine and for removing the ferric chloride by washing and drying; and using reaction vessels of relatively substantial volume in order to achieve long residence times, as the chlorination reaction under such conditions is relatively slow.

It has, surprisingly, been found that the reaction for chlorinating trichloroethylene, and therefore for removing same, is accelerated under the influence of the presence of ethylene. This favorable action on the part of ethylene is all the more unexpected since the simultaneous chlorination of the ethylene to 1,2-dichloroethane results in the formation of only a minimal amount, in fact an insignificant amount, of 1,1,2-trichloroethane, such amount being, for example, less than 0.10% by weight.

According to the invention, the reaction for chlorinating trichloroethylene is effected continuously in a homogeneous reaction zone into which 1,2-dichloroethane containing trichloroethylene, ethylene, and chlorine are continously introduced at a temperature of from 20° to 80° C., protected from light radiation, in the presence of a Lewis catalyst, preferably ferric chloride, the ethylene/trichloroethylene molar ratio being at least 50 and the trichloroethylene/chlorine molar ratio being at most 0.02.

In accordance with a particular embodiment of the invention, the ethylene/trichloroethylene molar ratio is from 90 to 110. It has been found that the trichloroethylene chlorination reaction occurs more rapidly when the above ratio is higher than 90. For these values, the limit value of the increase in the speed of chlorination is observed, such that values which are greatly higher than 110 do not afford any particular advantage over values which are higher than, but close to, 90. For values lower than 90, it has been observed a smaller increase in the speed of the reaction for chlorinating trichloroethylene to pentachloroethane, the increase tending toward zero when the ethylene/trichloroethylene molar ratio tends toward 50.

Moreover, in accordance with the invention it is advantageous for chlorination to be carried out with a trichloroethylene/chlorine molar ratio which is from 0.009 to 0.011.

The chlorine which is introduced in the molecular state into the homogeneous reaction zone is dissolved in the reaction medium and its concentration should be maintained at from 0.5 to 20 g per kilo of liquid of the reaction medium, and preferably from 2 to 10 g per kilo.

The molecular chlorine used according to the invention can either be in liquid form which is gasified before reaction, or in the form of gaseous chlorine in the raw state, such as is collected at the outlet from works for manufacturing chlorine by the electrolysis of aqueous solutions of sodium chloride. Thus, it is virtually equivalent to use liquid chlorine in a state of 99.9% purity, or a chlorine in a state of 95% purity, the main impurities being $CO_2$, $O_2$, $N_2$, $H_2$ and $CO$. These gases are inert under the operating conditions of the reaction. The chlorine used can be diluted by inert gases such as the gases just mentioned above. Such dilution in a diluent/chlorine molar ratio which can reach 1/1 is not harmful to the reaction.

It is advantageous for chlorination to be effected at a temperature which is from 40° to 60° C., and with an amount of Lewis acid as catalyst of from 20 to 800 parts per million by weight of the reaction medium and preferably from 60 to 200 parts per million. In the case of anhydrous ferric chloride, it can either be introduced into the homogeneous zone as such, or formed in situ by inter-reaction of the chlorine with the walls which are made of steel or other iron alloys which are subject to attack by chlorine, or with iron turnings or iron oxides introduced into said zone.

In accordance with a particular feature of the invention, the amount of moisture which can be present in the homogeneous zone is advantageously less than 200 parts per million by weight of the liquid reaction medium and, more particularly, less than 80 parts per million.

In accordance with an embodiment of the invention, in the case of ferric chloride used as the catalyst, the liquid reaction medium has a $FeCl_3/H_2O$ molar ratio which is at least equal to 1.

It has been found that pressure does not have an influence on the chlorination reactions which occur in the homogeneous reaction zone.

Having described the basic concepts of the invention, reference is now made to the following examples which are provided by way of illustration, but not of limitation, of the practice of the invention.

EXAMPLE 1

The chlorination reaction is carried out in a homogeneous reaction zone represented by a cylindrical reaction vessel of ordinary steel, provided with a heat-regulation system for maintaining the temperature in the interior of the reaction vessel at a constant value. This system comprises a circulating pump whose output can vary from 200 to 800 liters/hour and which draws in the liquid 1,2-dichloroethane at the bottom of the reaction vessel and passes it through an exchanger in the top of the reaction vessel. The reaction vessel is provided with a system for varying the height of the overflow, which amounts to varying the working volume of the reaction vessel. The gases which are liable to escape at the top of the reaction vessel pass through a discharge condenser, then through two columns which are sprinkled with water and sodium hydroxide for respectively removing hydrochloric acid and chlorine which may possibly be present in the discharge gases. The reaction vessel temperature is fixed at 60° C. and the following are continuously introduced, in the absence of light radiation, being drawn in by the pump:

750 g per hour of a 1,2-dichloroethane containing approximately 10 parts per million by weight of moisture (water), 200 parts per million by weight of ferric chloride, and 1% by weight of trichloroethylene, that is to say, 7.5 g per hour or 0.057 mole per hour;

4.28 moles per hour of chlorine in a state of 97% purity ($CO$, $CO_2$, $N_2$, $H_2$, $O_2$ are the main impurities);

4.2 moles per hour of ethylene.

The concentration of chlorine dissolved in the reaction liquid is maintained at about 3.7 g per kg after the working volume of the reaction vessel has been fixed at 3.83 liters, which corresponds to a residence time of 4 hours.

The $C_2H_4/C_2HCl_3$, $C_2HCl_3/Cl_2$ and $FeCl_3/H_2O$ molar ratios are respectively equal to about 73.6, 0.013, and 2.2.

After 18 hours of reaction, there is continuously collected a 1,2-dichloroethane, analysis of which shows that 94% of trichloroethylene has been converted into pentachloroethane.

The amount of 1,1,2-trichloroethane produced was approximately 0.09% by weight with respect to the 1,2-dichloroethane produced.

FIRST COMPARATIVE TEST

In order to show what the trichloroethylene chlorination reaction becomes in the absence of ethylene, Example 1 was repeated, except that the feed of chlorine was 0.086 moles per hour and that of ethylene was zero, the $C_2HCl_3/Cl_2$ molar ratio being approximately 0.66 and the $C_2H_4/C_2HCl_3$ molar ratio being zero. The concentration of dissolved chlorine was maintained at approximately 3.7 g per kg of reaction liquid. The working volume of the reaction vessel was adjusted to 2.5 liters so as to correspond to a residence time of 4 hours as in Example 1. After 18 hours of continuous operation, analysis of the 1,2-dichloroethane which was continuously discharged showed that only 78% of the trichloroethylene had been converted into pentachloroethane, and that it contained about 3.7 g per kg of dissolved chlorine.

SECOND COMPARATIVE TEST

Example 1 was repeated, except that instead of 4.2 moles per hour of ethylene there was introduced about 1.10 moles per hour, which corresponds to a $C_2H_4/C_2HCl_3$ molar ratio of about 19.3, and instead of 4.28 moles per hour of chlorine, 1.12 moles per hour was introduced, which gives a $C_2HCl_3/Cl_2$ molar ratio of about 0.05. The concentration of dissolved chlorine was maintained at about 3.7 g per kg of reaction liquid. The height of the overflow was so set as to provide a working volume of about 2.83 liters, which corresponds to a residence time of 4 hours. After 18 hours of reaction, it was found that only about 78% of the trichloroethylene introduced was converted.

THIRD COMPARATIVE TEST

It was desired to attempt, without using ethylene, to attain a rate of conversion of trichloroethylene to pentachloroethane of 94%, this being the result of Example 1. The operating conditions were those of the first comparative test described above. It was observed that the working reaction volume had to be 8.2 liters, which corresponds to more than double that of Example 1 to obtain the same result as that example.

EXAMPLE 2

Into the reaction vessel as described in Example 1 but in which the reaction volume is set at 4.5 liters, there is introduced at a temperature of 60° C., being drawn in by the pump, 750 g per hour of dichloroethane containing less than 15 parts per million by weight of water and 1% by weight of trichloroethylene. 6.34 moles per hour of chlorine and about 6.2 moles per hour of $C_2H_4$ are introduced into the reaction vessel so as to provide 3.7 g per kg of chlorine dissolved in the dichloroethane. The $C_2H_4/C_2HCl_3$ molar ratio and the $C_2HCl_3/Cl_2$ molar ratio are respectively 108.8 and 0.009 approximately. The $FeCl_3/H_2O$ molar ratio is approximately 2. After 18 hours, after analysis of the 1,2-dichloroethane which is discharged continuously from the reaction vessel, it is calculated that the rate of conversion of trichloroethylene is 97%. The amount of 1,1,2-trichloroethane produced sas 0.09% by weight with respect to the 1,2-dichloroethane produced.

By way of comparison, to produce a rate of trichloroethylene conversion of 97%, under the conditions of the first comparative test of Example 1, that is to say, in the absence of ethylene, the working reaction vessel volume had to be 16 liters.

EXAMPLE 3

Into the reaction vessel of Example 1, but in which the reaction volume was set at 4.83 liters, there is introduced at a temperature of 60° C., in addition to the 750 g per hour of 1,2-dichloroethane containing 1% of trichloroethylene and 20 parts per million by weight of water, 7.55 moles per hour of 97% pure chlorine and 7.3 moles per hour of $C_2H_4$, so as to provide a concentration of dissolved chlorine in the vicinity of 3.7 g per kg. The $C_2H_4/C_2HCl_3$, $C_2HCl_3/Cl_2$, and $FeCl_3/H_2O$ molar ratios in the reaction liquid are respectively 129, 0.007 and 2 approximately. After 18 hours, the 1,2-dichloroethane is analyzed and it is found that 97% of the trichloroethylene has been converted. The amount of 1,1,2-trichloroethane produced was 0.09% by weight with respect to the 1,2-dichloroethane produced.

It will be understood that various changes and modifications can be made in the details of formulation, procedure, and apparatus without departing from the spirit of the invention, especially as defined in the following claims.

We claim:

1. In the process for reducing the amount of trichloroethylene which is present as an impurity in 1,2-dichloroethane through chlorination of trichloroethylene in the liquid phase into pentachloroethane at a temperature in the range from 20 to 80°C in the absence of light and in the presence of a Lewis acid catalyst the improvement wherein ethylene is introduced with chlorine and 1,2-dichloroethane containing trichloroethylene in a homogeneous reaction zone, with the mole ratio of the ethylene to trichloroethylene of at least 50 and the mole ratio of trichloroethylene to chlorine of at most 0.02.

2. A process according to claim 1 wherein the ethylene/trichloroethylene molar ratio is from 90 to 110.

3. A process according to claim 1 wherein the trichloroethylene/chlorine molar ratio is from 0.009 to 0.011.

4. A process according to claim 1 wherein the chlorine which is dissolved in the reaction medium is maintained at a concentration of from 0.5 to 20 g per kilo of liquid of the reaction medium and preferably from 2 to 10 g per kilo.

5. A process according to claim 1 wherein the liquid phase in the homogeneous reaction zone contains less than 200 parts per million by weight of moisture.

6. A process according to claim 1 wherein the Lewis acid is in an amount of from 60 to 200 parts per million by weight of the liquid in the homogeneous reaction zone.

7. A process according to claim 5 wherein the Lewis catalyst/moisture molar ratio is at least equal to 1.

* * * * *